United States Patent
Suzuki

(10) Patent No.: US 7,187,749 B2
(45) Date of Patent: Mar. 6, 2007

(54) BLUR COMPENSATION APPARATUS FOR X-RAY IMAGE AND MEDICAL X-RAY IMAGING APPARATUS USING THE BLUR COMPENSATION APPARATUS

(75) Inventor: Masakazu Suzuki, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 194 days.

(21) Appl. No.: 10/424,043

(22) Filed: Apr. 24, 2003

(65) Prior Publication Data

US 2003/0215051 A1    Nov. 20, 2003

(30) Foreign Application Priority Data

Apr. 24, 2002  (JP) .............................. 2002-122471
Apr. 22, 2003  (JP) .............................. 2003-116583

(51) Int. Cl.
  *G21K 1/12*  (2006.01)
  *H05G 1/28*  (2006.01)

(52) U.S. Cl. ........................ 378/19; 378/162; 378/165

(58) Field of Classification Search ................. 378/4, 378/19, 95, 8, 39, 38, 40, 62, 162–165; 250/370.09
See application file for complete search history.

(56) References Cited

U.S. PATENT DOCUMENTS 5,023,894 A * 6/1991 Yamashita et al. ............ 378/4
5,784,429 A * 7/1998 Arai ............................. 378/38
6,018,563 A * 1/2000 Arai et al. .................... 378/39
6,092,928 A * 7/2000 Mattson et al. ............. 378/205
6,510,196 B2 * 1/2003 Laner .......................... 378/39

* cited by examiner

*Primary Examiner*—Edward J. Glick
*Assistant Examiner*—Irakli Kiknadze
(74) *Attorney, Agent, or Firm*—Koda & Androlia

(57) ABSTRACT

A blur compensation apparatus for X-ray image of an object to be examined used for a medical X-ray imaging apparatus, which has an X-ray generator and an X-ray imaging device opposite to the X-ray generator, said X-ray generator and said X-ray imaging device interposing therebetween said object held by an object holding means, wherein a sensor means for detecting blur movement of said object is provided near an objective projection position on said object holding means, and wherein a blur compensation process is executed for the X-ray image obtained by said X-ray imaging device, based on a positional change information which is calculated from a detection signal detected by said sensor means during X-ray radiography, said positional change information being the positional change amount with respect to said objective projection position relative to a reference position previously specified on said object holding means.

8 Claims, 10 Drawing Sheets a) image flame

F#1   F#2   F#i ----- F#n b) sensor detection signal
   positional change amount e1    e2    ei ----- en c) image blur E(1)    E(2)    E(i) ----- E(n)

d) zoom rate

MFe(1)    MFe(2)    MFe(i) ----- MFe(n)

e) compnesated image frame

F#1   F#2   F#i ----- F#n

BLUR COMPENSATION APPARATUS FOR X-RAY IMAGE AND MEDICAL X-RAY IMAGING APPARATUS USING THE BLUR COMPENSATION APPARATUS

FIELD OF THE INVENTION

The present invention relates to a blur compensation apparatus for X-ray image used for a medical X-ray imaging apparatus for obtaining an X-ray image of an object having an X-ray generator and an X-ray imaging device opposite to the X-ray generator, the X-ray generator and the X-ray imaging device interposing the object held by an object holding means, and relates to a medical X-ray imaging apparatus using the blur compensation apparatus.

PRIOR ART

In an X-ray imaging apparatus wherein an X-ray CT, a flat plane tomography or a curved plane tomography is executed while an object is held by an object holding means and an X-ray generator and an X-ray imaging device are relatively moved (including rotation) to the object interposing the object, the obtained X-ray image isn't always preferable because the object moves for the object holding means, namely object image blur movement.

This problem is remarkable in case of radiography when the object is moved, however, even when the object isn't moved, it is difficult for the object, which is being a living body, to remain stationary for a fixed time, so that it has been also a problem to be solved.

Specifically, in an X-ray CT in which a three dimensional X-ray absorption coefficient is produced by subjecting the sequentially obtained images to backprojection, the sequential images are reflected by the object image blur movement which gradually changes and such images give an adverse effect on the X-ray absorption coefficient obtained by backprojection. Therefore, this problem has been important in the X-ray CT and also in an X-ray panoramic radiography in which the sequentially obtained images are patched to produce one image.

Therefore, several means and methods have been proposed to solve the object image blur movement.

For example, JP-A-2000-217810 proposes a conical X-ray beam CT apparatus wherein an obtained X-ray transmitted image is divided into plural groups having different sizes to calculate the clearness of each X-ray distribution images obtained by reconstructing the X-ray transmitted image per each group and an X-ray sectional image or a three dimensional X-ray image of an object is obtained using the X-ray transmitted image of the group having the largest clearness.

This blur compensation method doesn't require a sensor for detecting an object image blur movement, however the X-ray transmitted image with lower clearness isn't used because of the blur movement. In case that the object isn't moved, such a method has been available because the blur movement rate is small. On the other hand, when the object is moved, the X-ray transmitted image with preferable clearness has seemed not to be obtained because the blur movement rate is large.

The medical imaging apparatus described in JP-A-2001-120528 has a detection means of an object image blur movement in such a manner that an X-ray radiography is executed when the object movement detected by the detection means becomes smallest. Therefore, it has been also available for a radiography with the object fixed, but its effectiveness hasn't been confirmed in case of an X-ray radiography with the object moved because when the blur movement becomes smallest isn't specified.

According to the CT apparatus described in JP-A-11-253433, an X-ray impermeable positioning marker is provided for an object and the blur compensation amount is calculated by the position of the image of the positioning marker. Such an apparatus has been useful for the blur compensation process on the imaging plane but hasn't been useful for the blur compensation process in a direction perpendicular to the imaging plane, namely blur compensation process of a zoom rate of the image.

In the data compensation apparatus in the CT apparatus described in JP-B-6-16099, a marker is provided for an object and is monitored by a TV camera to obtain rotation angle signals as body movement data, thereby the data being used for the compensation of the image layer data.

According to this method, it is required to mark each time and is troublesome to mark the object other than to position the object at a projection start position.

TV camera and so on are required to be provided so as to face the object in addition to the object holding means so that the space for the camera is necessary. Generally, the apparatus itself for obtaining and analyzing the image needs a relatively large space. Specifically, comparing with an acceleration sensor and an angular speed sensor, the difference of the required space is remarkable. Further, an accurate marker recognition on a comparatively difficult image has to be achieved because the marking position is detected by the projected image, thereby arising a possibility of low accuracy. In addition, plural TV cameras are required for detecting a three dimensional body movement so that a larger space is required.

The present invention is proposed to solve the above-mentioned problems and the object of the invention is to provide a blur compensation apparatus for X-ray image which can effectively carry out object image blur movement compensation during X-ray radiography not only when the object isn't moved but also when the object is moved and which is useful for a blur compensation process not only on a projection plane but also on a zoom rate of an image and to provide a medical X-ray imaging apparatus using this blur compensation apparatus.

SUMMARY OF THE INVENTION

According to one embodiment of the blur compensation apparatus for X-ray image of an object to be examined used for a medical X-ray imaging apparatus, which has an X-ray generator and an X-ray imaging device opposite to the X-ray generator, the X-ray generator and the X-ray imaging device interposing therebetween the object held by an object holding means, a sensor means for detecting blur movement of the object is provided near an objective projection position on the object holding means, and a blur compensation process is executed for the X-ray image obtained by the X-ray imaging device, based on a positional change information which is calculated from a detection signal detected by the sensor means during X-ray radiography, the positional change information being the positional change amount with respect to the objective projection position relative to a reference position previously specified on the object holding means.

The blur compensation apparatus for X-ray image has the sensor means for detecting an object image blur movement around the objective projection position on the object holding means, thereby detecting the positional change at the objective projection position for the reference position of the object holding means. In other words, the sensor means is provided around the objective projection position on the object holding means, not for the object, so that the sensor means isn't required to be replaced per each object, resulting in saving of labor.

For example, when the object holding means is comprised of a chair and a head fixing means on the upper part of the chair, the sensor means is provided for the head fixing means, the reference position is set on the chair, and the detection data of the sensor means is considered to be the positional change at the objective projection position (head) for the chair (reference position). Therefore, the setting of the sensor means for detecting the positional change of the objective projection position (head) is completed only by fixedly holding the head of the object by the head fixing means like the conventional X-ray radiography.

In addition the three-dimensional variation at the objective projection position can be detected by thus detecting the positional change at the objective projection position, thereby enabling to execute the blur compensation process in more multidimensional using the data comparing with the prior art.

Further, the sensor means is provided for the object holding means for holding and moving the object in case of moving the object, therefore, the sensor means is moved together with the object and the relative blur movement of the object against the object holding means can be always detected.

Hence, even when the object is moved, the blur movement at the objective projection position can be detected without being affected by the whole movement of the object.

Because the sensor means is provided for the object holding means, other preparation isn't required than positioning of the object at a projection start position, thereby reducing the burden of an operator. In addition, detection means need not to be provided other position than the object holding means, so that the system can be made compact.

If an acceleration sensor, an angular speed sensor, and an angle sensor which can execute two-dimensional or three-dimensional detection are used for the sensor means, more accurate and compact construction can be achieved.

In those cases, the sensor means preferably detect two-dimensionally or three-dimensionally in the directions orthogonal each other. One sensor means capable of two-dimensional detection or three-dimensional detection may be provided or plural sensor means capable of two-dimensional detection or three-dimensional detection may be provided.

Preferably, the sensor detects two-dimensionally the two directions orthogonal each other on the moving plane, namely two-dimensionally in an X direction and a Y direction which are parallel to the moving plane and is orthogonal each other, when the object and the imaging system comprised of the X-ray imaging device and the X-ray generator are relatively moved.

More specifically, the moving plane refers to the plane on which the X-ray imaging device and the X-ray generator are moved so as to describe an arc when they are turned around the object in case of tomography.

As for tomography on a curved plane, it may be constructed such that the patient, namely an object, moves against the X-ray imaging device and the X-ray generator while fixing the rotation center. The plane on which the moving orbit of the objective projection position of the object exists is one of the moving plane.

In addition to the above-mentioned two-dimensional detections, the sensor may detect three-dimensionally also in one more direction perpendicular to the moving plane, namely in a Z-direction orthogonal to each one of the X-direction and the X-direction which are orthogonal each other.

In the above-mentioned, two orthogonal directions on the moving plane are shown as a preferable embodiment of two-dimension, however, they may be set optionally other than this embodiment. Further, the two directions aren't always orthogonal each other and may be optional angle.

I case of adding one detection direction to the two directions, the one direction may not be orthogonal to the moving plane and may be set in optional direction.

Namely, the angle of the two or three directions may be optionally set as far as the blur amount is detected.

According to other embodiment of the blur compensation apparatus for X-ray image according to the present invention, the blur compensation apparatus executes the following steps; determining the existence of the blur movement of the object image with respect to a series of X-ray image frames produced when X-ray radiography is performed based on the positional change amount and/or zoom rate calculated from the detection signal detected by the sensor means; sequentially executing the blur compensation process for the X-ray image frame in which the blur movement of the object image is found at the determining step, based on the positional change amount and/or the zoom rate obtained by the sensor means; and rearranging and storing a series of X-ray image frames including the X-ray image frame of which blur movement is compensated as above, in time series order as in the X-ray radiography.

According to other embodiment of the blur compensation apparatus of the present invention, the sensor means comprises two acceleration sensors directing two different directions respectively, the two acceleration sensors detecting the accelerated velocity at the objective projection position, and wherein the positional change information is calculated based on the acceleration data by executing a dynamic processing as previously prepared.

In this blur compensation apparatus for X-ray image, the acceleration sensor is used as the sensor means to detect the acceleration at the objective projection position and the acceleration is considered to be an external force applied on the objective projection position, not being integrated, and the structure defining the objective projection position as a beam structure, so that the deflection caused on the beam structure by the external force is determined as the positional change at the objective projection position.

Therefore, the deflection of the beam structure, namely the positional change at the objective projection position, is easily calculated by the calculation formula of the beam deflection without executing a difficult integration.

Further, two acceleration sensors are used into two different directions respectively so that the two-dimensional blur movement is accurately detected without executing a difficult image processing for detecting the blur movement. In addition, the sensors are usually very small one capable of mounting on a fingertip, thereby enabling the apparatus more compact.

In case of detecting the three-dimensional blur movement other than the two-dimensional blur movement, all necessary is adding one sensor. Therefore, the apparatus can be constructed more compact comparing with the construction providing plural TV cameras. Angular speed sensor and an angle sensor may be provided similarly.

The calculation method of the positional change from the acceleration at the objective projection position as mentioned above is called a dynamic processing.

In this blur compensation apparatus for X-ray image, the acceleration sensor is provided in two directions, more preferably in two directions orthogonal each other, concretely or generally in two directions orthogonal in a horizontal direction, or in two directions orthogonal on a moving plane when radiography is executed while an object and an imaging system comprised of an X-ray imaging device and an X-ray generator are relatively moved, thereby enabling a two-dimensional blur compensation process.

The reason why the number of acceleration sensor is limited to two directions is that the blur movement in a direction orthogonal to the relative moving plane during radiography is only a little and the blur compensation process isn't necessary in case of a general imaging apparatus such as an X-ray panoramic radiography apparatus. If necessary, the acceleration sensor may be provided in three directions.

According to the other embodiment of the blur compensation apparatus of the present invention, the sensor means comprises two angular speed sensors provided in two different directions respectively, the two angular speed sensors detecting the angular speed of an angle of inclination at the objective projection position for the reference position, and the positional change information is calculated from the angular speed data.

This blur compensation apparatus for X-ray image is the same as the above-mentioned embodiment in that the structure defining the objective projection position is considered to be a beam construction. However, in this embodiment, the sensor means is comprised of an angular speed sensor. The angular speed sensor detects the angular speed of an angle of inclination at the objective projection position to obtain the angle of inclination at the objective projection position by integration. Further, the positional change at the objective projection position is calculated, thereby facilitating the arithmetic operation.

According to other embodiment of the blur compensation apparatus of the present invention, the sensor means comprises two angle sensors provided in two different directions respectively, the two angle sensors detecting an angle of inclination of the objective projection position for the reference position, and the positional change information is calculated from the angle data.

This blur compensation apparatus for X-ray image is also the same as the above-mentioned embodiment in that the structure defining the objective projection position is considered to be a beam construction. However, in this embodiment, the sensor means is comprised of an angle sensor. The angle sensor detects the angle of inclination at the objective projection position. Then, the positional change at the objective projection position is calculated, thereby facilitating the arithmetic operation.

According to other embodiment of the blur compensation apparatus of the present invention, the blur compensation apparatus calculates the blur movement on an imaging plane of the X-ray imaging device and the deviation of zoom rate based on the calculated positional change amount and executes the blur compensation process of the image obtained by the X-ray imaging device.

According to this blur compensation apparatus, because at least the two-dimensional positional change at the objective projection position is calculated by the sensor means, the positional change is reconstructed to calculate the blur movement of an X-ray image on the imaging plane of the X-ray imaging device and the blur movement orthogonal to the plane direction, namely the deviation of zoom rate of an X-ray image, thereby enabling the image blur compensation process. Therefore, the two-dimensional blur compensation process, which has been difficult in the prior art, becomes possible.

According to the other embodiment of the blur compensation apparatus of the present invention, the object holding means comprises a chair for holding a human object in sitting position and a head fixing part for fixedly holding the human head provided at an upper part of the chair, wherein the sensor means is provided at the head fixing part, and the reference position is set on the chair.

According to this blur compensation apparatus for X-ray image, the object holding means is practically defined wherein the setting position of the sensor means is set on the head fixing part and the reference position is on the chair. The sensor detects the positional change of the objective projection position which is a human head against the chair so that this compensation apparatus is preferably used for the radiography of the head, the jaw, the dental arch, and the tooth for a dental purpose.

According to one embodiment a medical X-ray imaging apparatus for obtaining an X-ray image of an object to be examined which has an X-ray generator and an X-ray imaging device opposite to the X-ray generator, the X-ray generator and the X-ray imaging device interposing therebetween the object held by an object holding means; the medical X-ray imaging apparatus comprises the blur compensation apparatus for an X-ray image, the blur compensation apparatus for X-ray image comprising a sensor means for detecting the blur movement of the object is provided near an objective projection position on the object holding means, and a blur compensation process is executed for the X-ray image obtained by the X-ray imaging device based on a positional change information which is calculated from the detection signal detected by the sensor means during X-ray radiography, the positional change information being the positional change amount with respect to the objective projection position relative to a reference position previously specified on the object holding means.

This medical X-ray imaging apparatus has the above-mentioned blur compensation apparatus for X-ray image so that it achieves the effects of the compensation apparatus.

According to other embodiment, the medical X-ray imaging apparatus further comprises an object moving means for moving the object holding means depending on the purpose of X-ray radiography.

According to this embodiment of the medical X-ray imaging apparatus, comparing with the above-mentioned apparatus, the object moving means is further provided. Namely, the object is moved (including rotation) during X-ray radiography so that the object image blur movement is often caused. Therefore, the effects of the above-mentioned blur compensation apparatus for X-ray image are achieved more effectively.

According to other embodiment of a medical X-ray imaging apparatus for obtaining an X-ray image of an object to be examined which has an X-ray generator, an X-ray imaging device opposite to the X-ray generator, the X-ray generator and the X-ray imaging device being rotatable around a rotation center, and a object moving means for moving the object holding means for holding the object at least in a direction parallel to the rotation plane of the rotation, the medical X-ray imaging apparatus can execute an X-ray CT radiography and an X-ray panoramic radiography; the medical X-ray imaging apparatus comprises a blur compensation apparatus for X-ray image, the blur compensation apparatus comprises the object holding means having a chair for holding a human object in sitting position and a head fixing part for fixedly holding the human head provided at an upper part of the chair, and a sensor means for detecting the blur movement of the object image is provided at the head fixing part and a reference position is set on the chair.

This medical X-ray imaging apparatus is a dental apparatus for executing an X-ray radiography of a human head. The apparatus has the blur compensation apparatus for X-ray image corresponding to the X-ray CT and the X-ray panoramic radiography in which the object is moved. The effect such that the X-ray CT and the X-ray panoramic radiography can be unified is more effectively achieved.

According to other embodiment of the medical X-ray imaging apparatus of the present invention, the blur compensation apparatus executes the following steps; determining the existence of the blur movement of the object image with respect to a series of X-ray image frames produced when X-ray radiography is performed based on the positional change amount and/or zoom rate calculated from the detection signal detected by the sensor means; sequentially executing the blur compensation process for the X-ray image frame in which the blur movement of the object is found at the determining step, based on the positional change amount and/or zoom rate obtained by the sensor means; and rearranging a series of X-ray image frames including the X-ray image frame of which blur movement is compensated as above, in time series order as in the X-ray radiography.

In this embodiment, the projected X-ray images are expanded in a series of image flames, the detection signal of the sensor means is allotted for each frame, and an image blur and the zoom rate are processed per each frame so that an X-ray radiography and a blur compensation process can be executed separately, thereby being applicable for the next process.

BRIEF DESCRIPTION OF THE DRAWINGS

FIG. 7a is its front view, and FIG. 7b is its side view.

DETAILED DESCRIPTION OF THE INVENTION

The preferred embodiments of the present invention will be explained referring to the attached drawings.

Figure 1:
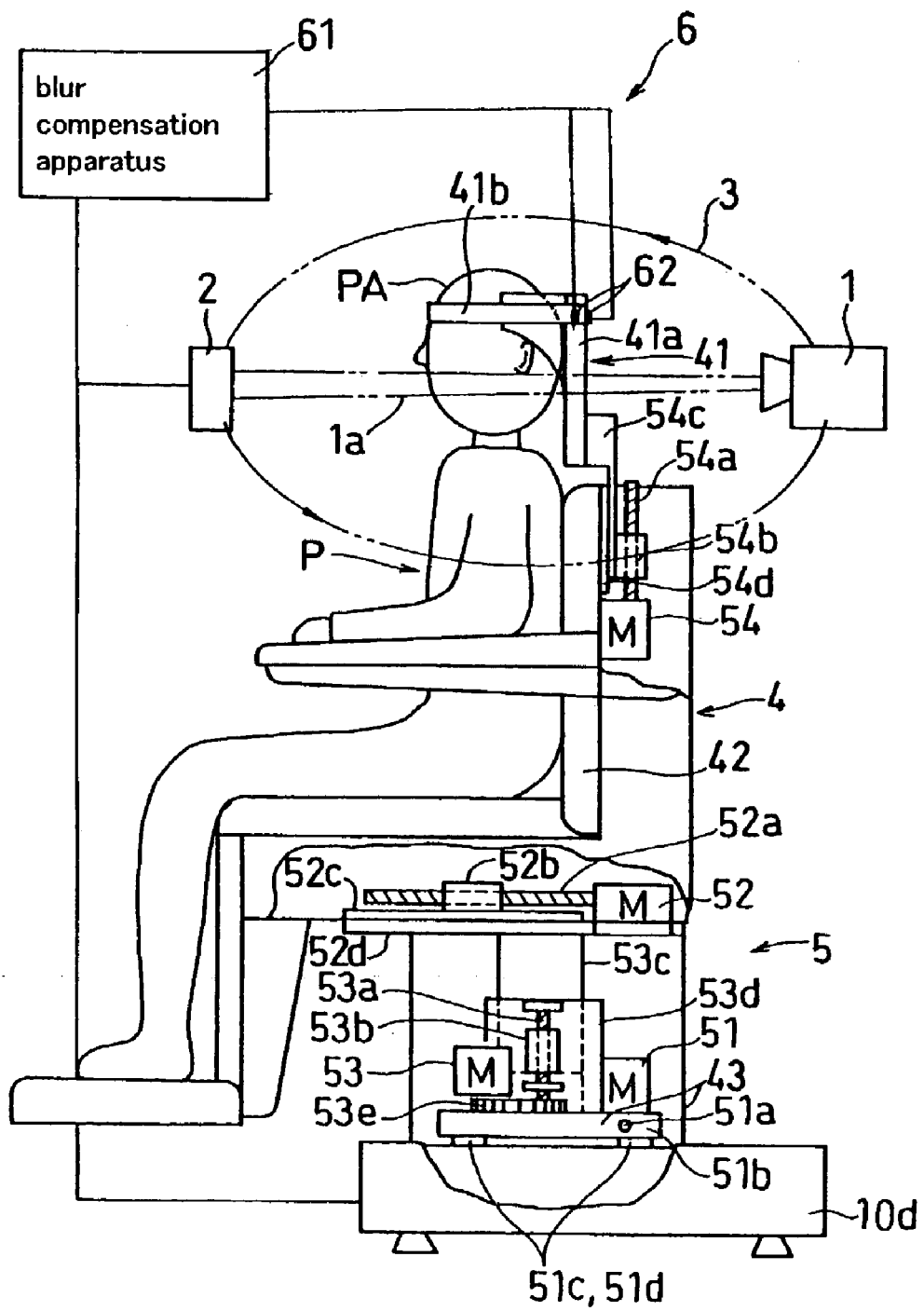
FIG. 1 shows an entire construction of one embodiment of a blur compensation apparatus for X-ray image according to the present invention.

FIG. 1 shows an entire construction of one embodiment of a blur compensation apparatus for X-ray image according to the present invention.

The blur compensation apparatus for X-ray image 6 is provided with an X-ray generator 1 and an X-ray imaging device 2 which is arranged to be opposite to the generator 1 interposing an object P held by an object holding means 4 and is used for a medical X-ray imaging apparatus 20 (see FIG. 6) to obtain an X-ray image of the object. The blur compensation apparatus for X-ray image 6 is further provided with an operation means for blur compensation 61 and a sensor means 62 for detecting the blur movement of the object P.

The X-ray generator 1 and the X-ray imaging device 2 are suspended from the both ends of a rotary arm 3, which is conceptually shown, so as to turn around the object P. When X-ray beam 1a is irradiated to the object P from the X-ray generator 1, the transmitted X-ray image is detected by the X-ray imaging device 2.

The object holding means 4 has a head fixing means 41 for holding and fixing a head PA of the object P, namely a patient, a chair 42 for holding the object P in sitting position, and a base 43 as the foundation. The object holding means 4 is placed on an object moving means 5 so as to move in the perpendicular direction and in the horizontal direction for the medical X-ray imaging apparatus 20 which is provided vertically.

The head fixing means 41 has a support pillar 41a standing on the back of the chair 42 and a fixing band 41b provided at the upper part of the pillar 41a to bind and fix the head PA of the object P. The support pillar 41a is vertically controllable against the chair 42 by means of a head fixing part moving motor 54 of the object moving means 5 so as to fix the head PA of the object P at an appropriate position.

The object moving means 5 is provided, as shown in the figure, inside or around the object holding means 4 and is comprised of an X-axis motor 51, a Y-axis motor 52, a Z-axis motor 53, and a head fixing part moving motor 54, all of which is a driving source. The object moving means 5 is also comprised of ball screw axes 51a, 52a, 53a and 54a which are driven to be rotated by each one of the above-mentioned motors, female screws 51b, 52b, 53b and 54b each one of which is screwed with the above screw axis respectively, male rails 51c, 52c, 53c and 54c each one of which is fixed with each female screw to be slid together, and the male rails 51d, 52d, 53d and 54d to slide the male rails accurately.

The X-axis motor 51, the ball screw axis 51a and the female rail 51d are fixed to a base 10d which is the foundation of the entire medical X-ray imaging apparatus 20. The female screw 51b and the male rail 51c are fixed to the base 43 of the object holding means 4. When the X-axis motor 51 is controlled to be driven and rotated, the object holding means 4 is moved in an X-direction against the base 10d (in a direction shown with an outlined arrow 51 in FIG. 8, namely from side to side).

The Z-axis motor 53, the ball screw axis 53a and the female rail 53d are fixed to the base 4c side of the object holding means 4, and the female screw 53b and the male rail 53c are fixed to the chair 42 side. When the Z-axis motor 53 is controlled to be driven and rotated, the chair 42 is moved in a Z-direction (in a direction shown with an outlined arrow 53 in FIG. 8, namely up and down) against the base 43 so as to control the height of the object for the rotary arm 3.

In this embodiment, because of the limitation of the area, a rotary driving force is transmitted in a Z-direction between the Z-axis motor 53 and the ball screw axis 53a by means of a timing belt 53e and a timing pulley (not shown). If the area isn't limited, they may be directly connected.

Also in this embodiment, the female rail 53d and the male rail 53c are comprised of a combination of a large diameter piston and cylinder so as to guide the up and down movement of the chair 42 on which the object is sitting and to make the blur movement of the chair 42 as small as possible against the base 43 when the chair 42 is moved horizontally.

The Y-axis motor 52, the ball screw axis 52a and the female rail 52d are fixed to the male rail 53c moving vertically against the base 43 of the object holding means 4 and the female screw 52b and the male rail 52c are fixed to the chair 42 side. When the Y-axis motor 52 is controlled to be rotated and driven, the chair 42 is moved in a Y-direction (in a direction shown with an outlined arrow 52 in FIG. 8, namely from back and forth) against the base 43.

The headrest motor 54, the ball screw axis 54a and the female rail 54d are fixed to the upper part of the back of the chair 42 of the object holding means 4 and the female screw 54b and the male rail 54c are fixed to the pillar 41a of the head fixing means 41. When the headrest motor 54 is controlled to be driven and rotated, the head fixing means 41 is moved in a Z-direction (in a direction shown with an outlined arrow 54 in FIG. 8, namely up and down) against the upper part of the chair 42.

The sensor means 62 of the blur compensation apparatus for X-ray image 6 in this embodiment is provided for the pillar 41a of the head fixing means 41 in the vicinity of an objective projection position PA of the object holding means 4, the position PA being the head of the object P, in order to detect the positional change amount of objective projection position PA against the chair 42 which is a reference position of the object holding means 4.

The operation means for blur compensation 61 executes a blur compensation process of the image obtained by the X-ray imaging device 2 based on the detection information of the positional change amount by the sensor means 62 during X-ray radiography. The X-ray imaging device 2 and the object moving means 5 are also connected to the operation means 61 as described later so that the blur compensation process can be executed based on the output from them.

According to the blur compensation apparatus for X-ray image 6, the sensor means 62 for detecting the blur movement of the object P is provided not for the object P but for the head fixing part 41 in the vicinity of the objective projection position PA on the object holding means 4 so that the sensor means 62 isn't required to be replaced per each object P.

Further, the sensor means 62 is provided for the head fixing part 41, its reference position is set to be the chair 42, and the detection data from the sensor means 62 are considered to be the positional change amount against the chair (reference position) 42 at the objective projection position (head) PA. Therefore, setting of the sensor means 62 for detecting the positional change amount of objective projection position (head) PA is completed only by holding and fixing the head PA of the object P by means of the head fixing part 41.

By detecting the positional change amount of objective projection position in the manner mentioned above, a three dimensional variation at the objective projection position can be detected, thereby achieving the blur compensation process in multidimensional based on the data comparing with the prior arts.

Further according to the blur compensation apparatus for X-ray image 6, when the object P is moved by means of the object moving means 5, the sensor means 62 is provided for the object holding means 4 which is moved with the object P held. Accordingly the sensor means 62 is also moved together with the object P so that the relative blur movement of the object P against the object holding means 4 is always detected. Even if the object P is moved, the blur movement at the objective projection position PA can be detected without being affected by the movement of the object P.

Figure 2A:
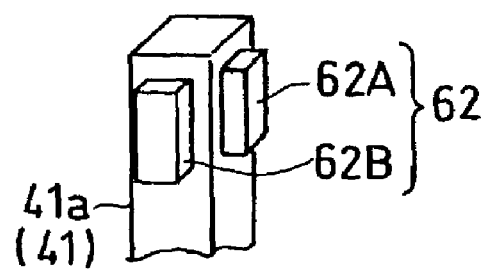
FIG. 2a is a conceptual view showing a sensor means of the present invention.
Figure 2B:
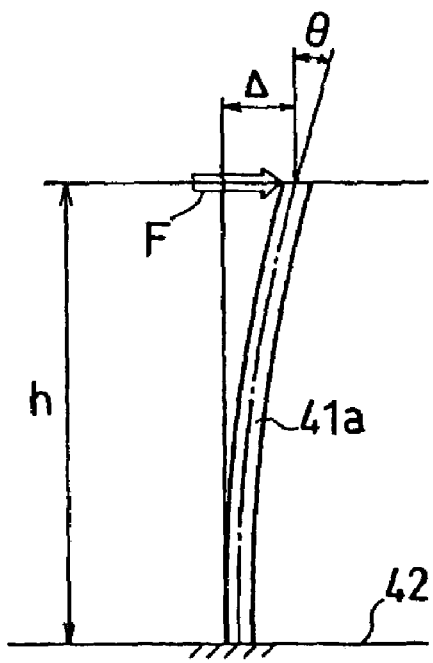
FIG. 2b is a conceptual view showing the relation of the output of the sensor means and the amount of positional change at the objective projection position.
Figure 2C:
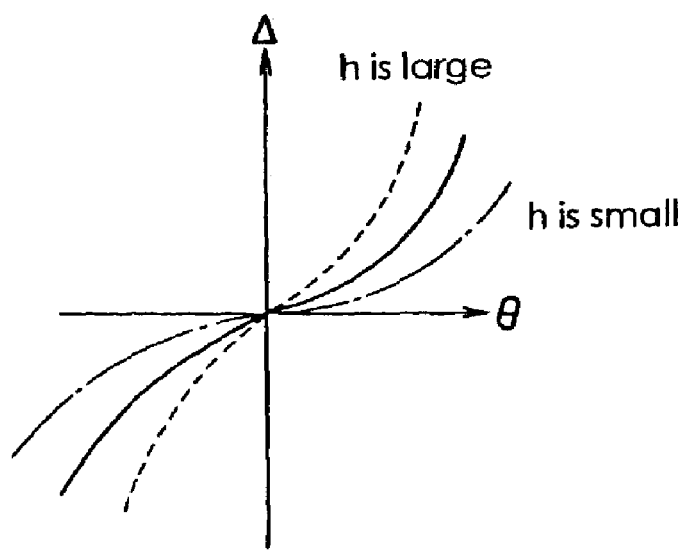
FIG. 2c is a graph showing the relation of FIG. 2c.

FIG. 2a is a conceptual view showing a sensor means of the present invention, FIG. 2b is a conceptual view showing the relation of the output of the sensor means and the amount of positional change at the objective projection position, FIG. 2c is a graph showing the relation of FIG. 2b. The members already explained have the same reference numbers and their explanations are omitted.

A general method for a detection means for detecting the amount of positional change of the object to be measured by attaching to the object itself is to provide an acceleration sensor and to subject the detection data to integration twice. In case of the object holding means 4, the sensor means is provided for the head fixing part 41 which is a structural beam against the chair 42 being a reference position, therefore, the positional change amount of head fixing part 41 against the chair 42 can be calculated by detecting the inclination of the structural beam. Further, an angle sensor and an angular speed sensor are also used.

The case when the sensor means 62 is comprised of an acceleration sensor is explained hereinafter.

The sensor means 62 is comprised of two acceleration sensors, 62A and 62B. They are provided for the upper side walls of the pillar 41a of the head fixing part 41 so as to be orthogonal each other in order to detect the acceleration in two directions.

The acceleration detected by each sensor means 62A and 62B is subjected to time integration. Because the sensor means 62A and 62B are provided for the head fixing part 41, when the object holding means 4 is moved, the affect by the movement is measured together. Therefore, it is required to attach an acceleration sensor to the chair 42 and to obtain the acceleration of the head fixing part 41 against the chair 42 by obtaining the difference of each output.

Otherwise, instead of providing an acceleration sensor for the chair 42, the acceleration caused by the movement may be obtained by calculation to get the acceleration of the head fixing part 41 for the chair 42 because the object holding means 4 moves following the object moving means 5.

If the acceleration is subjected to time integration, the amount of positional change of the head fixing part 41 against the chair 42 can be calculated, however, the integration is required to be executed by ignoring a direct current component because the blur movement at the objective projection position PA of the object P, namely vibration, is to be taken out.

However, in such a method by integration, operation isn't easy so that the inventors of the present invention propose a method by a dynamic operation as an easy method.

According to the dynamic operation method, the acceleration detected by each sensor means 62A and 62B is considered to be an external force applied on its setting position and the force is expressed by the reference numeral F as shown in FIG. 2b. Positional change amount Δ at the setting position is considered to be the deflection Δ when the external force F is acted on a cantilever beam comprised of the chair 42 and the pillar 41a.

If the length h is to the acting point of the external force F on the pillar 41a comprising the cantilever beam, the deflection (positional change amount) Δ is obtained by the following formula.

$$\Delta = F*h*h*h/(3*E*I) \qquad \text{deflection formula}$$

Wherein, "*" means multiplication, "/" means division, E refers to the modulus of longitudinal elasticity, and I refers to the geometrical-moment of inertia of the support pillar 41a. E and I are also called as a form factor and uniquely determined by the raw material and sectional shape of the pillar 41a.

As understood from the formula, when the acceleration detected by the sensor means 62A and 62B, namely the external force F, is found, the positional change amount Δ can be obtained by simple multiplication and division. In this description, only one of the sensors 62A and 62B which are positioned in orthogonal is considered.

The acceleration sensor of the blur compensation apparatus for X-ray image 6 is provided in two directions, preferably in directions orthogonal each other, specifically or generally orthogonal in the horizontal direction, or in two orthogonal directions on a moving direction of a moving plane during radiography while the object P and the imaging system comprised of the X-ray imaging device 2 and the X-ray generator 1 are relatively moved, therefore achieving the blur compensation process two dimensionally.

The reason of limiting two directions for providing the acceleration sensor is that in case of a general imaging apparatus, for example an X-ray panoramic radiography apparatus, the blur movement in a direction orthogonal to a relative moving plane during radiography is minute so that compensation isn't required. The acceleration sensors may be provided in three directions, if necessary. If the acceleration sensor is a three-axis type, only one sensor is provided. The numbers of the sensors may be applied to the case when the angular speed sensor and the angle sensor as described hereafter are used.

If the sensor means 62 is an angular speed sensor, each angular speed sensor 62A and 62B finds the angular speed of an angle of inclination θ of the head fixing part 41 (objective imaging position PA) against the chair 42, a reference position. The angle of inclination θ is obtained by subjecting the obtained angular speed data to time integration. In this case, like the case of the acceleration data, the direct current component is ignored. Gyroscope type sensors such as mechanical type, optical type, hydraulic type, vibration type and so on including a micro gyroscopic sensor may be used as an angular speed sensor.

If the sensor means 62 is an angle sensor, each angle sensor 62A and 62B directly finds the angle of inclination θ of the head fixing part 41 (objective projection position PA) against the chair 42, a reference position. In case of the angle sensor, the direct current component is also obtained, therefore achieving compensation including the direct current component. A joint type angle sensor or a tape type angle sensor may be used.

In either case of the angular speed senor and the angle sensor, the support pillar 41a in this embodiment, the structure for defining the objective projection position, is understood as a beam structure and the positional change amount Δ at the objective projection position is obtained by the angle of inclination θ of the pillar 41a (head fixing part 41) against the chair 42. The relation is shown in FIG. 2b in which the positional change amount Δ is obtained as the function of the angle of inclination θ and the length h of the support pillar h.

The function is shown in the form of graph in FIG. 2c.

If the angular speed sensor and the angle sensor are used as the sensor means 62, such an operation can be easily executed.

Strain gauge or a semiconductor strain gauge for measuring the stress by strain may be provided instead of an acceleration sensor, an angular speed sensor and an angle sensor to calculate the external force F from the measured stress and to obtain the positional change amount of objective projection position from the above-mentioned deflection formula.

Figure 3:
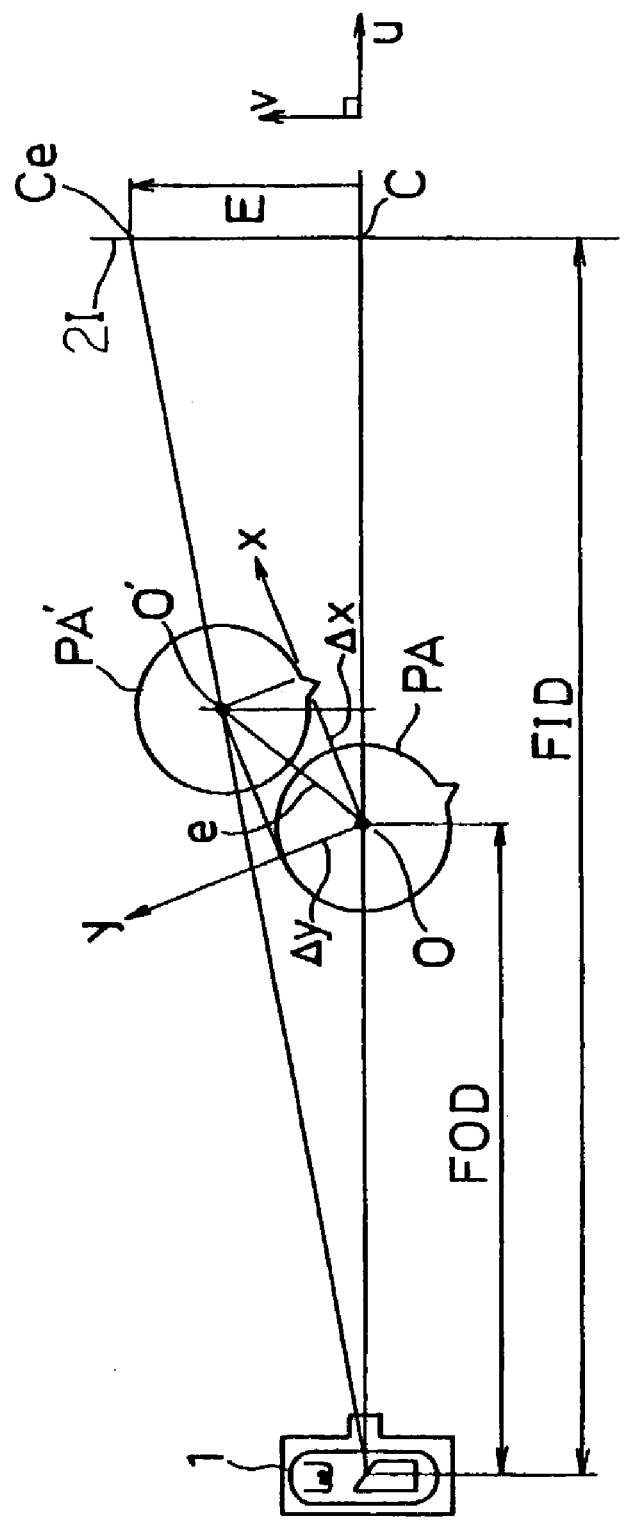
FIG. 3 is an explanatory view of the relation among thus obtained positional change amount at the objective projection position, the blur movement on the imaging plane and the zoom rate blur.

FIG. 3 is an explanatory view of the relation among thus obtained positional change amount at the objective projection position, the blur movement in a flat direction on the imaging plane and the deviation of the zoom rate due to blur movement of the object.

In the figure, 2I shows an imaging plane of the X-ray imaging device 2, O shows the center of the objective projection position PA (head of the object P) without blur movement, O' shows the center of the objective projection position PA' in case of causing blur movement, x-y shows a coordinate system wherein x and y refer to orthogonal directions where the sensor means 62A and 62B as shown in FIG. 2 are provided respectively when the center O is an origin, Δx and Δy are positional change amount in an x-direction and in y-direction obtained by the detection information of the sensor means 62A and 62B respectively, and e shows the positional change amount combined with Δx and Δy.

Also in the figure, the reference C shows an intersection of the imaging plane 2I and a perpendicular line (X-ray beam) extending from the X-ray generator 1 through the center O of the objective projection position PA, without blur movement, into the imaging plane 2I and the numeral "Ce" is an intersection of the imaging plane 2I and a straight line (X-ray beam) extending from the X-ray generator 1 through the center of O' of the objective projection position PA', when blur movement is caused, into the imaging plane 2I.

The reference "FOD" shows the distance from the X-ray generator 1 to the center O without blur movement, "FID" shows the distance from the X-ray generator 1 to the imaging plane I, "E" shows the image blur movement in an imaging plane direction on the imaging plane 2I, "u" is a unit vector in a direction away from the X-ray generator 1 and in a direction perpendicular to the imaging plane 2I when the intersection C is an origin, and "v" is a unit vector perpendicular to the unit vector u and in a direction into the intersection Ce.

As understood from the figure, the image blur movement E and the zoom rate Mfe of the image affected by the positional change amount e (affected by bye blur movement in a direction perpendicular to the image blur movement E)

can be obtained form the positional change amount e of the objective imaging position PA.

Accordingly, the zoom rate MF of the center 0 of the objective projection position PA without blur movement is expressed by the following formula.

$$MF=FID/FOD$$

On the other hand, the zoom rate MFe considering the blur movement of the object, namely the zoom rate MFe considering the positional change amount e, is expressed by the following formula.

$$MFe=FID/(FOD+e*u)$$

Further, the image blur movement E is expressed with the following formula.

$$E=MFe*e*v$$

In case of X-ray CT in which backprojection is carried out by continuously using the obtained images and in case of X-ray panoramic radiography wherein a curved sectional image is produced by patching the obtained images, the affect of the zoom rate error is large so that the zoom rate MFe and the image blur movement E are both considered. Otherwise, in simpler way, only the image blur movement E may be considered.

The zoom rate blur can be understood as the difference between the zoom rate MF without blur movement and the zoom rate MFe with blur movement.

Figure 4:
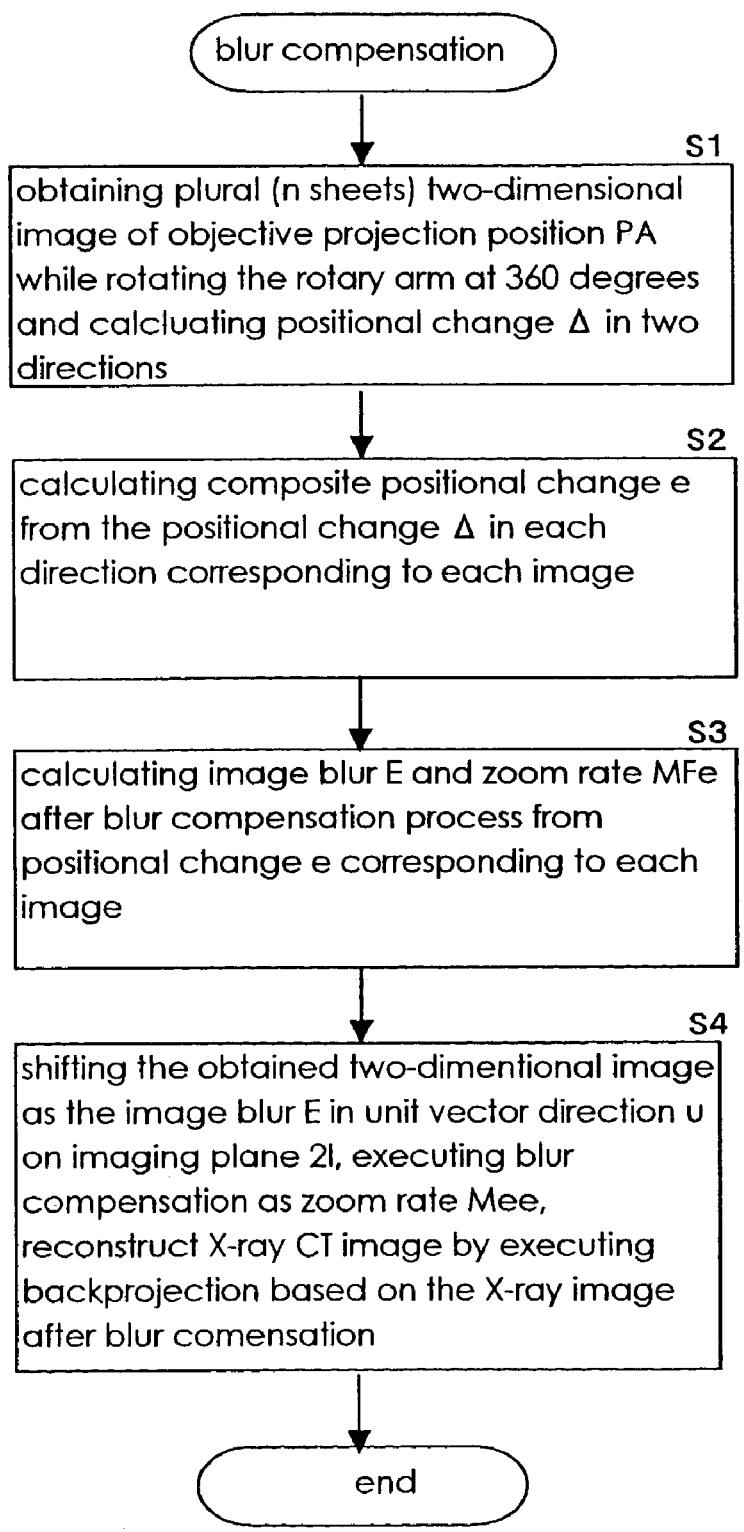
FIG. 4 is a flow chart showing procedures of the blur compensation process according to the present invention.

FIG. 4 is a flow chart showing the blur compensation procedure according to the present invention. Referring to this flow chart, the blur compensation procedure in case of X-ray CT will be explained hereinafter.

While turning a rotary arm at 360 degrees, X-ray beam 1a is irradiated to the objective projection position PA of the object P from the X-ray generator 1 to obtain plural numbers of two dimensional images (n sheets) of the objective projection position PA. In this case, the positional change amount Δ in each direction is calculated based on the detection information from the two sensor means 62A and 62B provided for the head fixing part 41 at each projection as explained referring to FIG. 2 (S1).

Next, the composite positional change amount e is calculated from the positional change amount Δ in each direction corresponding to each image (S2).

From thus obtained positional change amount e, the image blur movement E on the imaging plane 2I of the X-ray imaging device 2 and the zoom rate MFe after the blur compensation process are calculated for each image as explained referring to FIG. 3 (S3).

The obtained two dimensional image is shifted by the image blur movement E into a direction of a unit vector u on the imaging plane 2I to execute the blur compensation process as the zoom rate MFe and backprojection is executed based on the X-ray image after the blur compensation process to reconstruct the X-ray CT image (S4).

In case of other X-ray radiography such as an X-ray panoramic radiography, blur compensation procedures are the same.

Figure 5:
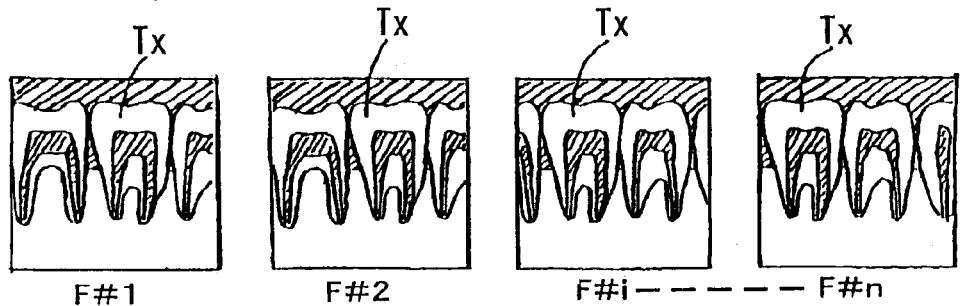
FIG. 5 shows a basic principle of the blur compensation process.
Figure 5:
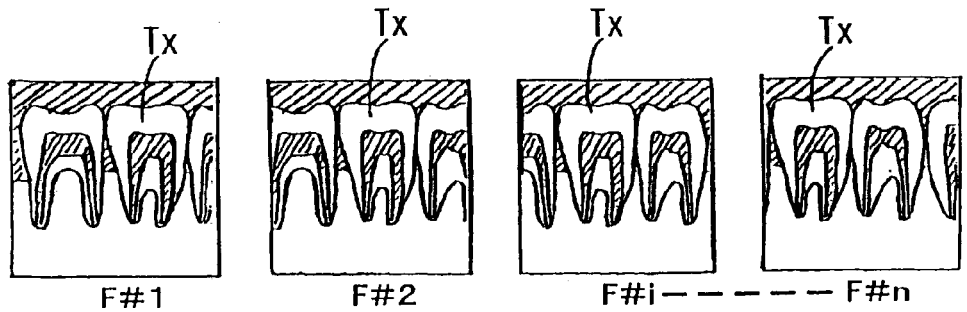

FIG. 5 shows a basic principle of the blur compensation operation.

FIG. 5 is an example of CT radiography. In case of CT, radiography is executed while turning the X-ray generator and the X-ray imaging device with the rotation center fixed on the objective projection position so that the X-ray image is obtained by gradually changing the angle sequentially and regularly for the objective projection position.

Figure 5A:
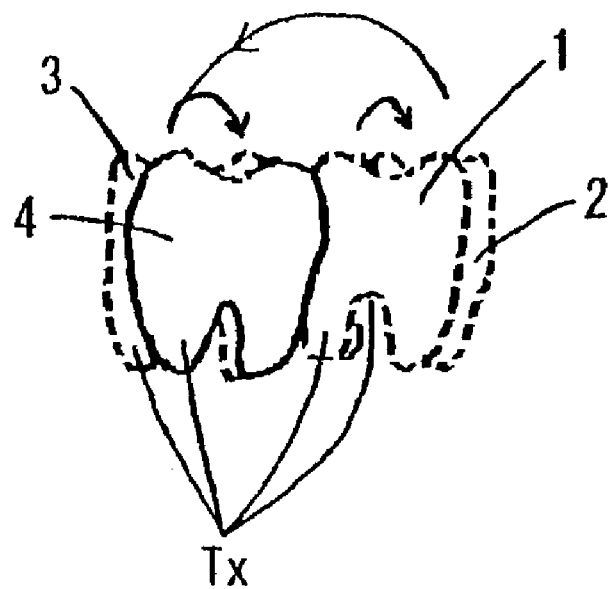
FIG. 5Aa is one example of the image frame before executing compensation process and FIG. 5Ab is one example of the image frame after executing compensation process.
Figure 5A:
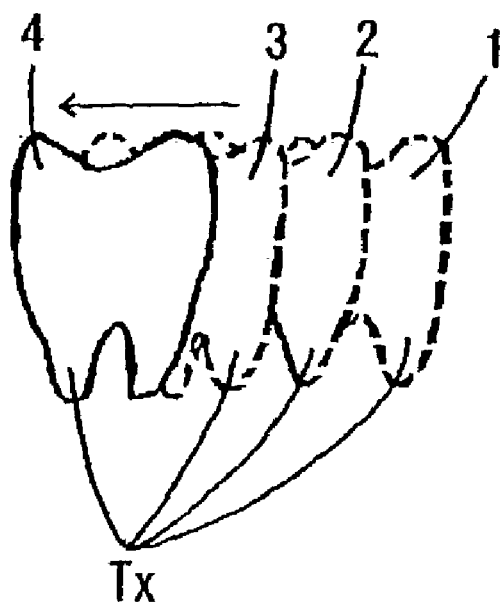

FIG. 5Aa is one example of the image frame before executing compensation process and FIG. 5Ab is one example of the image frame after executing compensation process.

More specifically, FIG. 5Aa shows an image flame before compensation and is moved back and forth against the X-ray radiation direction. This is the irregular movement mentioned above. After executing the blur compensation, the tooth Tx regularly moves in a fixed direction (from right to left in the figure) smoothly following the radiation direction.

The obtained X-ray images are produced in a series of frames, F#1, F#2, . . . F#n. The positional changes e1, e2 . . . en are calculated based on the detection signal of the sensor means 62 detected at the projection of each image frame F#1, F#2, . . . F#n. Further, the image blur movements E(1), E(2), . . . E(i) . . . E(n) which are the blur amount for the corresponding image and the zoom rate MFe(1), MFe(2), . . . MFe(i) . . . MFe(n) are calculated base on the calculated positional changes e1, e2 . . . en. Here, a specific tooth Tx is noticed among the image frames before compensation F#1, F#2, . . . F#n shown in item a) in the figure.

The image frame F#1, F#2, . . . F#n are images without blur movement as shown in item e) in the figure, in which the tooth Tx moves in the compensated image frames regularly from right to left with the constant change amount as shown in the item e). In contrast, it can be understood that the tooth Tx before compensation as shown in item a) in the figure moves with an irregular change amount. This irregular movement change is blur movement.

The calculation result of the blur movement E(1), E(2), . . . E(i) . . . E(n) and the zoom rate MFe(1), MFe(2), . . . MFe(i) . . . MFe(n) are compared to the threshold prepared in advance to determine the existence of blur movement.

Then, the image frame . . . F#i' . . . in which the blur movement of the object image is found at the determining step and a predetermined blur compensation process is executed after extracting the image frame.

Namely, the frame F#i' is returned as that the objective projection position PA is out of alignment with the reference position based on the calculated positional change ei. Further, the object image is varied (scaling up and down) so that the calculated zoom rate meets the predetermined one.

According to the above-mentioned procedure, after the image frame F#i' causing blur movement is compensated, the compensated image frame F#i is included in the projected series of image frames F#1, F#2, . . . , F#n so that they are rearranged and stored in time series of projection to prepare the image processing thereafter.

As mentioned above, when the sensor is designed to detect any one of the X-direction, the Y-direction and the Z-direction, the blur compensation based on the positional change amount in three directions is similarly executed and the blur compensation by zooming is executed according to the zoom rate if necessary. The blur movement in the Z-direction is generally only a little and doesn't work with the blur movement in the X-direction and the Y-direction, rather it occurs by accident. Therefore, the positional change amount in the Z-direction is detected separate from those of the X-direction and the Y-direction and it is enough the Z-direction compensation is done based on the detected positional change amount or followed by the zoom rate if necessary.

Figure 6:
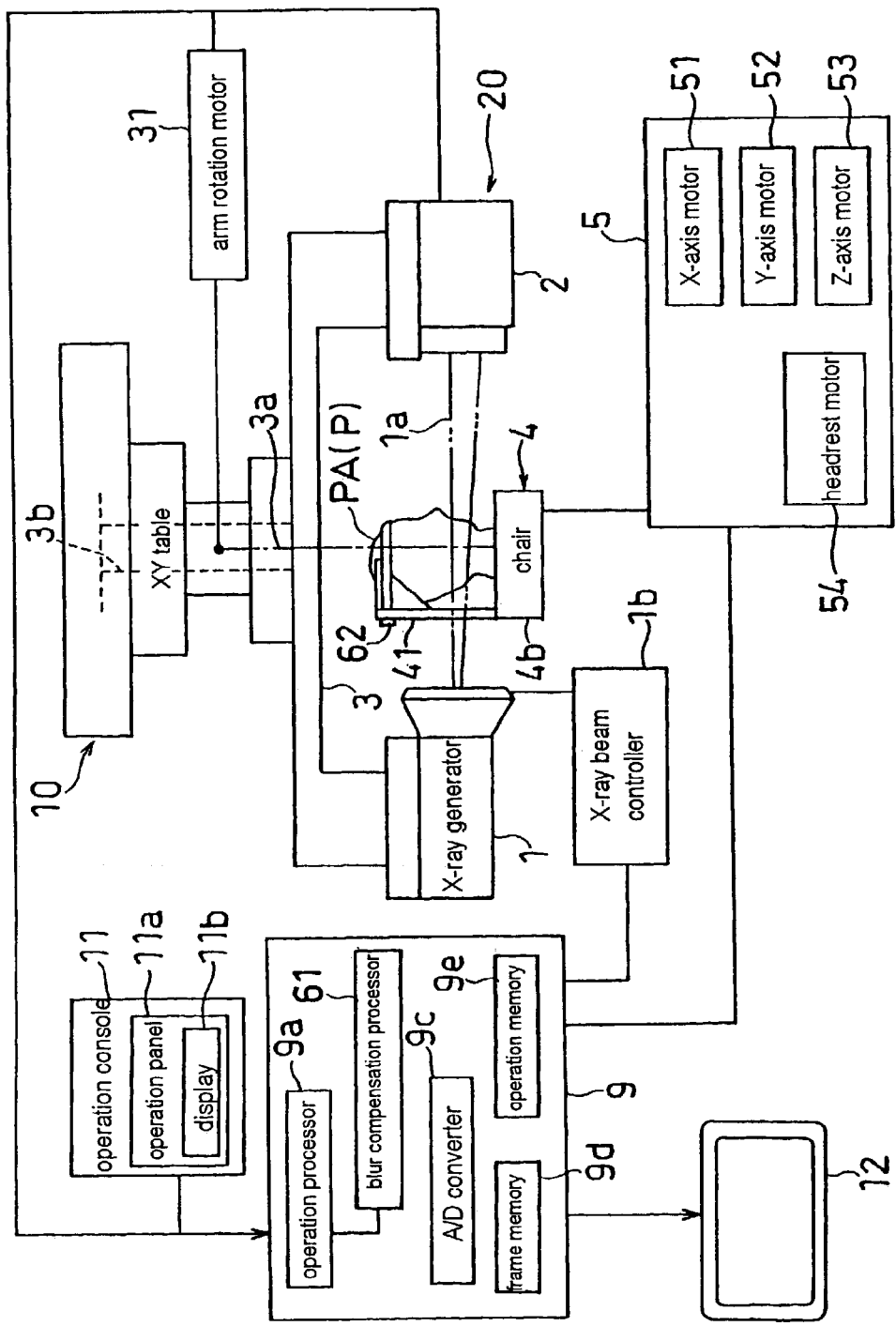
FIG. 6 shows an entire construction of one embodiment of a medical X-ray imaging apparatus using the blur compensation apparatus for X-ray image according to the present invention.

FIG. 6 shows an entire construction of one embodiment of a medical X-ray imaging apparatus using the blur compensation apparatus for X-ray image according to the present invention.

The medical X-ray imaging apparatus 20 is a local X-ray CT apparatus with a panoramic radiography function. The apparatus 20 has a rotary arm 3 from which an X-ray generator 1 and an X-ray imaging device 2 are suspended facing each other, an object holding means 4, an object moving means 5, an operation unit for blur compensation 61 and a sensor means 62, both comprising a blur compensation apparatus for X-ray image 6, an image processing means 9 for entirely controlling the apparatus, a main frame 10, and an operation console 11 having a display means 11b for showing operation guides in a simple manner for operating the apparatus 20 and an operation panel 10e for executing radiography following the display on the display means 11b.

The X-ray generator 1 has an X-ray beam controller 1b which controls the energy of the generated X-ray beam to irradiate the X-ray beam 1a with a desired beam width.

The X-ray imaging device 2 receives and detects the X-ray irradiated from the X-ray generator 1 and transmitted through the object and outputs the X-ray transmitted image data as analog electric data or as digital data in case of having an A/D converter itself. Two dimensional X-ray image sensor such as a cadmium telluride detector (CdTe) and a MOS sensor, a CCD image sensor which is a combination of a scintillator, a glass fiber, and the CCD, XII, and XICCD may be used. In this case, XII is used to output analog data.

In the XII, the X-rays run into a scintillator layer provided on the surface is converted into a visible light and the visible light is converted into electron to be electrically intensified by a photoelectric converter and the electron is converted to a visible light by a fluorescent material to be pictured by a two dimensionally arranged CCD camera (solid-state image sensing device) through a lens.

If a two dimensional image sensor which entirely detects the object's head is used, X-ray radiography can be done regardless of a local area in case of CT. However, if X-ray CT is executed in the light of minimizing the X-ray exposure, it is necessary to irradiate X-rays only on a projection interested area. In such a case, the X-ray radiation area is minimized by means of the X-ray beam controller 1b which defines the shape of the X-ray beam irradiated from the X-ray generator 1.

The rotary arm 3 is designed such that the X-ray rotation center 3a doesn't move into X, Y and Z directions, namely in horizontal or vertical, and a rotary motor 31 is only provided so as to turn the rotary arm 3 at a constant velocity or a variable velocity around the X-ray rotary center 3a.

The X-ray rotary center 3a of the rotary arm 3, namely a rotary axis, is provided vertically and the rotary arm 3 turns horizontally to locally irradiate conical X-ray beam 1a horizontally, enabling to construct a vertical apparatus with a small occupied area.

The rotary motor 31 constructs a rotary drive means of the rotary arm 3. Any motors which can control the rotary speed and rotary position of the rotary arm 3 can be used, for example, a servo motor and a pulse motor. The motor is directly connected with an axis to the X-ray rotary center 3a of the rotary arm 3.

Accordingly, the rotary arm 3 is turned around the rotary center 3a and the rotational position is known along a time axis, thereby being convenient for taking out the X-ray transmitted image by means of the X-ray imaging device 2 and enabling X-ray CT effectively without causing runout.

A hollow part 3b is provided for the rotation center 3a of the rotary arm 3. It is required to make a hollow part for all the members provided on the rotation center 3a in order to have such a hollow part 3b. For this purpose, a servo motor with a hollow axis can be used as a rotation control motor 31.

The hollow part 3b is provided to arrange connection wires between the X-ray generator 1 and the X-ray imaging device 2 suspended from the rotary arm 3, the operation console 11 of the main frame 10, and the image processing means 9.

The method for arranging the wire becomes a problem in order to provide an electric wring for rotating members. If the connection wire is thus arranged through the rotation center 3a of the rotary arm 3, affection caused by rotation such as twist can be minimized and a preferable effect such as a beautiful appearance can be obtained.

The object P sits on the chair 42 with its head fixed at the head fixing part 41 and calibration is carried out so as to conform the projection reference point of the object P and the projection reference point of X-ray radiography by means of the object moving means 5. In case of X-ray radiography on a curved plane, the object is moved along a predetermined orbit during rotary radiation of X-ray. In case of CT, the rotary center 3a of the rotary arm 3 is conformed to the projection interested area inside of the object P.

The projection interested area refers to an area inside of the objective projection position PA of the object P and X-ray beam 1a is irradiated on the area to be a target to be subjected to X-ray CT.

According to the object holding means 4, a patient sits on the chair 42 with his head fixed with the head fixing part 41 to radiograph the head as an objective projection position, thereby being utilized preferably as a vertical radiograph apparatus.

In case of a horizontal apparatus, the object holding means becomes a bed type for horizontally supporting a bed-ridden patient and moves the bed in X, Y, and Z directions. Further in case of a horizontal apparatus, the axial direction of the rotary axis of X-ray rotary radiation becomes horizontal, unlike vertical in a vertical apparatus.

The image processing device 9 has an operation processing means 9a constructed with an operation processor operable at high speed for image process analysis, a blur compensation operation means 61 as one function of the operation processing means 9a, an A/D converter 9c, a frame memory 9d, and an operation memory 9e.

Display selection means 12 is comprised of for example a personal computer to display a curved X-ray sectional image or a sectional image obtained by X-ray CT after the blur compensation process by the image processing device 9.

The display selection means 12 also has a communication function to transmit data accumulated via a public phone line and so on, specifically a curved X-ray sectional image obtained by the X-ray CT apparatus 20 or a sectional image obtained by X-ray CT, to other apparatus, and to receive required data and images from other apparatus. Further, the display selection means 12 is provided with an external recording medium reproducer to record and store the above-mentioned data and X-ray sectional images of a curved area or a plane area in a floppy disk, MO, DVD, CDR, CDRW and so on.

The image processing device 9 is constructed as mentioned above and is connected with the X-ray generator 1, the X-ray imaging device 2, motors 31, 51, 52, 53, 54, the operation console 12 and the display selection means 12 respectively to process data sent from these devices and to execute the blur compensation process, thereby achieving control.

More specifically, the image data received from the X-ray imaging device 2 is subjected to the blur compensation process by the blur compensation operation means 61 by means of the detected information from the sensor 62 to be converted into digital signals by the A/D converter 9c and the digitalized image data are stored in the frame memory 9d.

Plural image data in the frame memory 9d are stored in the operation memory 9e and a predetermined operation is executed according to a projection mode such as an X-ray tomography on a curved plane, an X-ray tomography on a flat plane, and an X-ray CT. Then sectional images are produced or a three-dimensional X-ray absorption coefficient on the projection interested area is calculated. Several images are reconstructed from thus obtained three-dimensional X-ray absorption coefficient to be shown on the display selection means 12 or are stored in an external memory means (not shown).

The image processing device 9 controls the X-ray beam controller 1b, motors 31, 51, 52, 53, 54 by the operation processing means 9a so that the conical X-ray beam irradiation from the X-ray generator 1, the rotation of the rotary arm 3 and the movement of the object moving means 5 corresponding to the rotation are controlled.

The X-ray beam controller 1b executes control to vary the shape of the X-ray beam irradiated from the X-ray generator 1 to the X-ray imaging device 2. For example, the beam is long in case of X-ray tomography on a curved plane, and is a rectangular in case of CT.

If the light receiving area of the X-ray imaging device 2 is small, radiography is repeated by changing the height of the object holding means 4 by means of the Z-axis motor 53 to add the obtained data.

Figure 7:
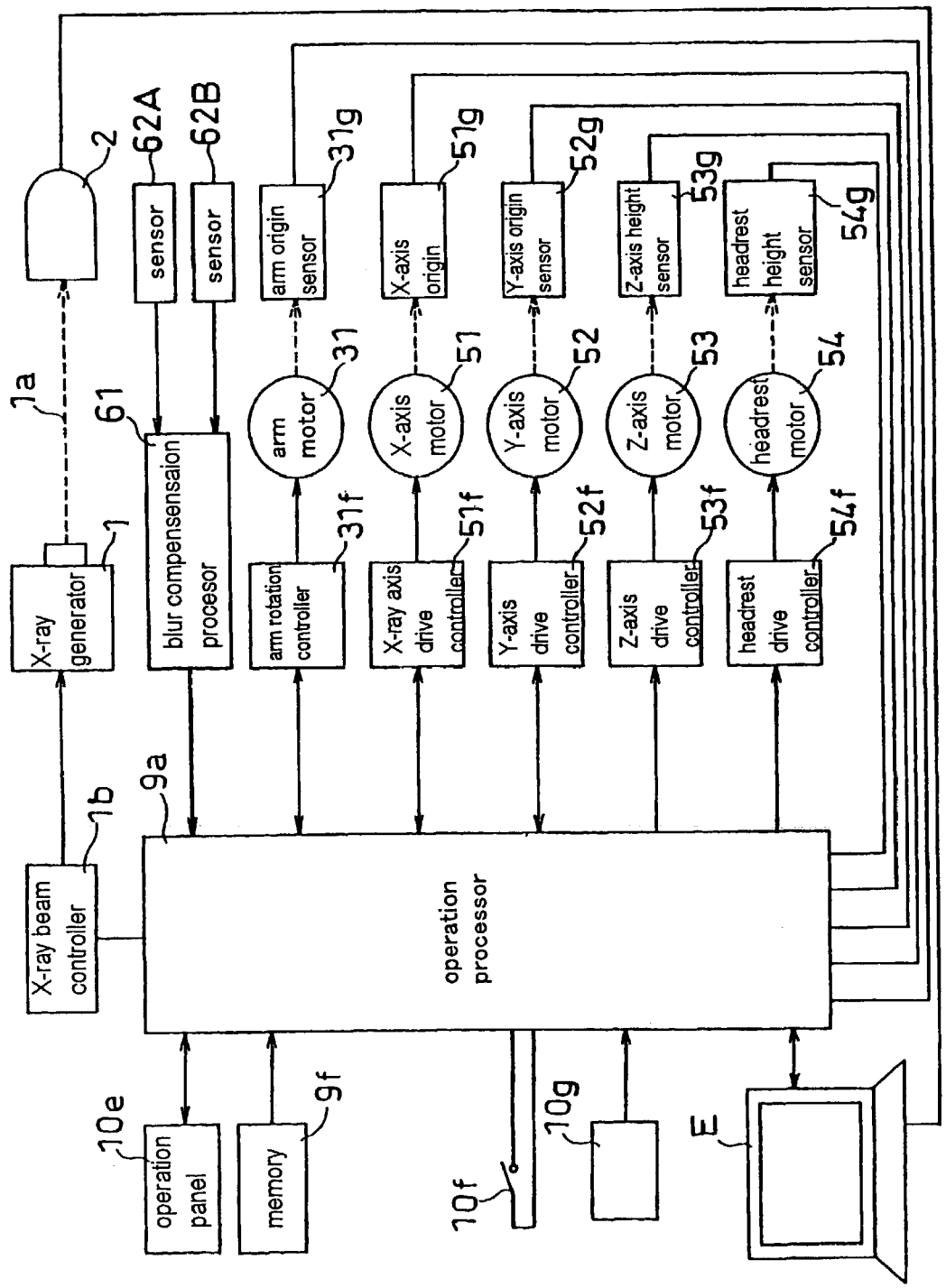
FIG. 7 shows a control diagram of a blur compensation process in a medical X-ray imaging apparatus of the present invention.

FIG. 7 is a control diagram referring to the blur compensation process for a medical X-ray imaging apparatus according to the present invention.

FIG. 7 takes out parts referring to the control of X-ray rotary radiation, the movement of the object and the blur compensation process of the object image from FIG. 6 showing the entire construction to show in detail.

The arm motor 31, the X-axis motor 51, the Y-axis motor 52, the Z-axis motor 53, and the headrest motor 54 are connected to the operation processing means 9a via an arm rotation controller 31f, an X-axis drive controller 51f, a Y-axis driving controller 52f, a Z-axis drive controller 53f and a headrest driving controller 54f respectively.

Arm origin detection sensor 31g, an X-axis origin detection sensor 51g, a Y-axis origin detection sensor 52g, aZ-axis origin detection sensor 53g and a headrest height detection sensor 54g are provided for the driven side such as a rotary arm 3 and so on driven by these motors 31, 51, 52, 53, 54 and those output is sent to the operation processing means 9a.

The blur compensation operation means 61 constructing a blur compensation apparatus for X-ray image 6, and the sensor means 62A and 62B are connected with the operation processing means 9a to execute the blur compensation process in association with irradiation data and movement data as mentioned hereinbefore.

The operation processing means 9a is connected with a memory 9f to record and store the apparatus control data and a program, an irradiation switch 10f being a start switch for X-ray radiation, and a remote control device 10g to execute necessary operations by remote control.

According to the above-mentioned construction, the operation processing means 9a carries out the X-ray rotary radiation control, the movement control of the object and the blur movement control of the object image.

Figure 8B:
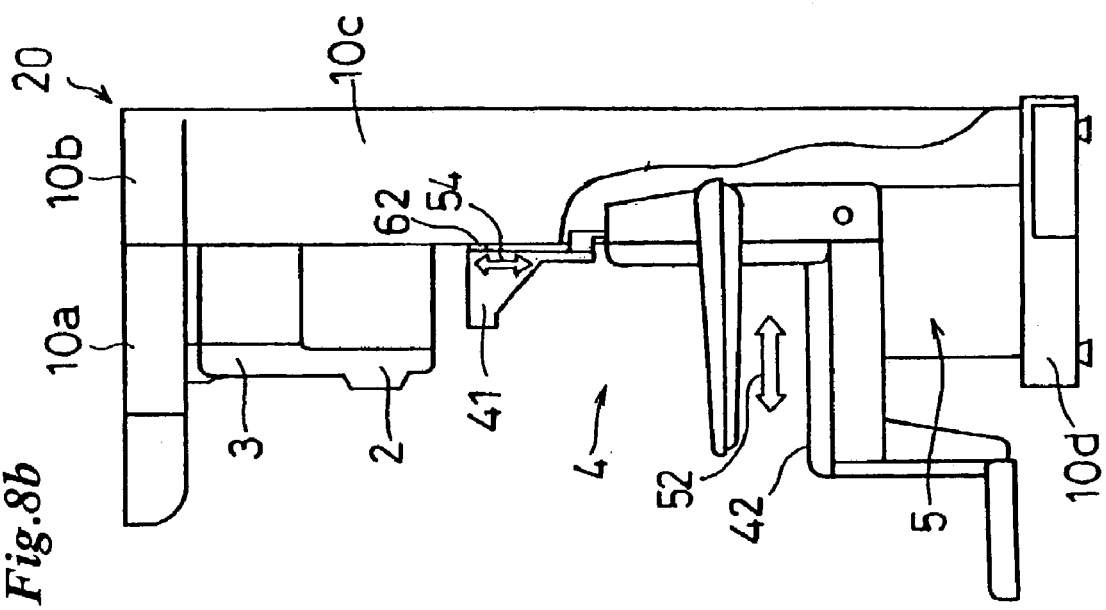
FIG. 8 shows an external view of a medical X-ray imaging apparatus of the present invention.
Figure 8A:
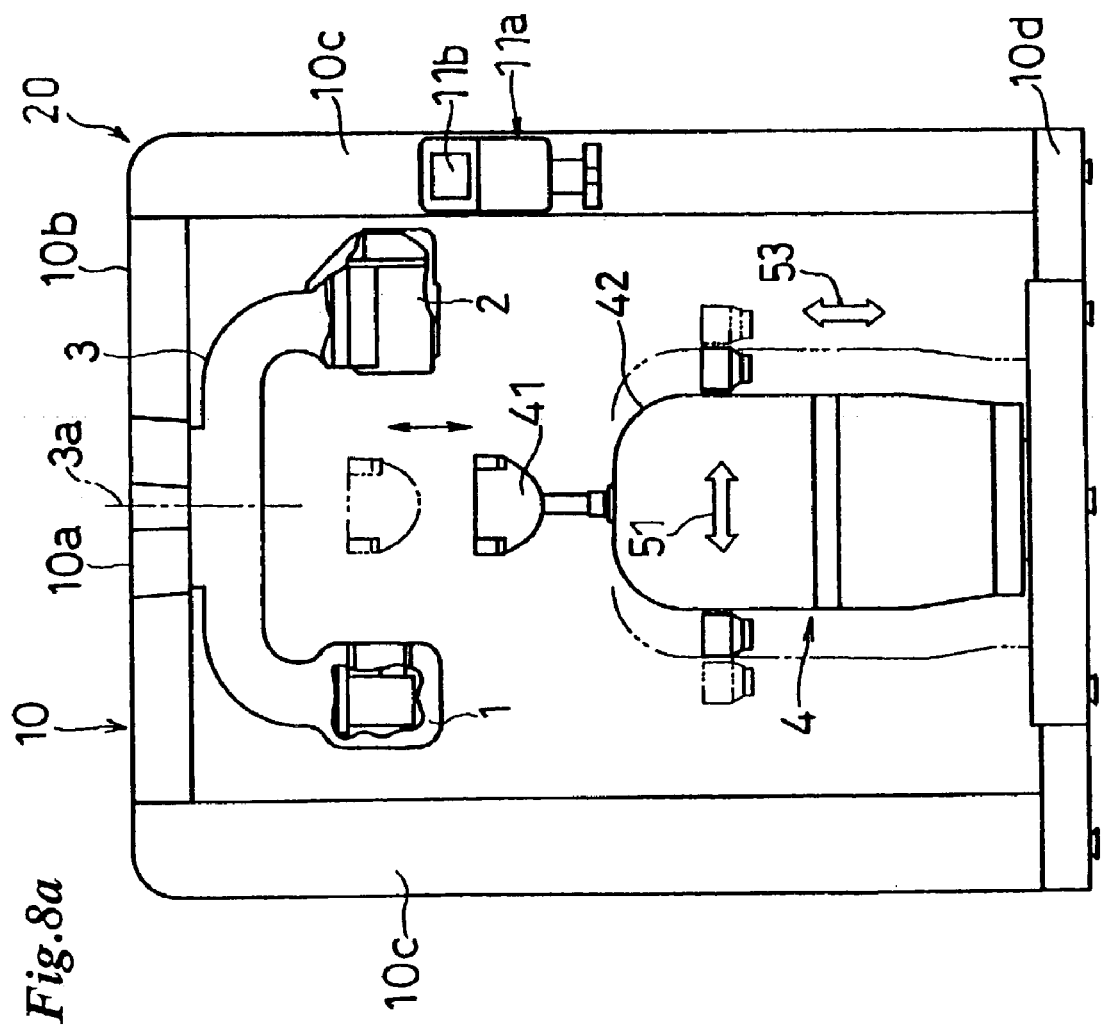

FIG. 8 shows an external view of a medical X-ray imaging apparatus of the present invention, FIG. 7a is its front view, and FIG. 7b is its side view.

According to the medical X-ray imaging apparatus 20, the X-ray generator 1, the X-ray imaging device 2, the rotary arm 3, the object holding means 4, the object moving means 5, the sensor means 62 consisting the blur compensation apparatus for X-ray image 6, and the operation panel 11a with the display 11b are provided for the main arm 10 as mentioned hereinbefore.

The display 11b is provided on the surface of a vertical beam 10c which is one of main frame 10 and on the operation panel 11a arranged where an operator easily uses the panel 11a while standing. The display 11b shows a dental jaw model and a guide display for operation.

Movement switch (not shown) is provided for the operation panel 11a to move the chair 42 side to side, back and forth or up and down by means of the object moving means 5. The object moving means 5 is also used to conform the reference position of X-ray radiography and a projection position of the object by means of the switch.

The main frame 10 is comprised of an arm 10a rotatably supporting the rotary arm 3, a cross beam 10b fixing the foundation of the arm 10a, a pair of vertical beams 10c supporting the cross beam 10b, and a base 10d on which the pair of vertical beams 10c are fixed and which is the foundation of the entire apparatus 20.

A highly rigid steel material is used for the members of the main frame 10 and braces and angular reinforcing members are appropriately used for resisting deformation so as not to vary the rotation center 3a of the rotary arm 3 during rotation.

The main frame 10 is constructed not to cause the rotary deflection of the rotary arm 3, so that it is applicable for the X-ray CT apparatus which requires no rotary deflection.

In this figure, the X-axis motor 51, the Y-axis motor 52, the Z-axis motor 53 and the backrest motor 54 constructing the object moving means 5 for moving the object holding means 4 for holding a patient, as explained referring to FIG. 1, are conceptually shown with outlined arrows with the same reference numerals.

As mentioned above, in this medical X-ray imaging apparatus 20, although the imaging system comprising the X-ray generator 1 and the X-ray imaging device 2 turns around the object, the X-ray rotation center 3a itself is strongly fixed so as not to move. On the other hand, a tomography on a curved plane (including dental X-ray panoramic radiography) becomes possible by moving the object holding means 4 holding the object P by means of the object moving means 5.

According to the medical X-ray imaging apparatus 20, an X-ray radiography is made possible by moving the object unlike the prior art in which the imaging system is moved. In such a case the object image blur movement is highly caused so that the effect of the apparatus of the present invention having a blur compensation apparatus for X-ray image is achieved advantageously.

Further, the medical X-ray imaging apparatus 20 uses a two-dimensional X-ray semiconductor image sensor which can sequentially store the continuously received X-ray images and reconstruct them. Combining the movement of the object and the rotatable imaging system, in principle, the apparatus 20 can execute any X-ray tomography including a sectional tomography on a flat plane. In such a case, the effect of the apparatus with the blur compensation apparatus for X-ray image according to the present invention can be effectively achieved.

Figure 9:
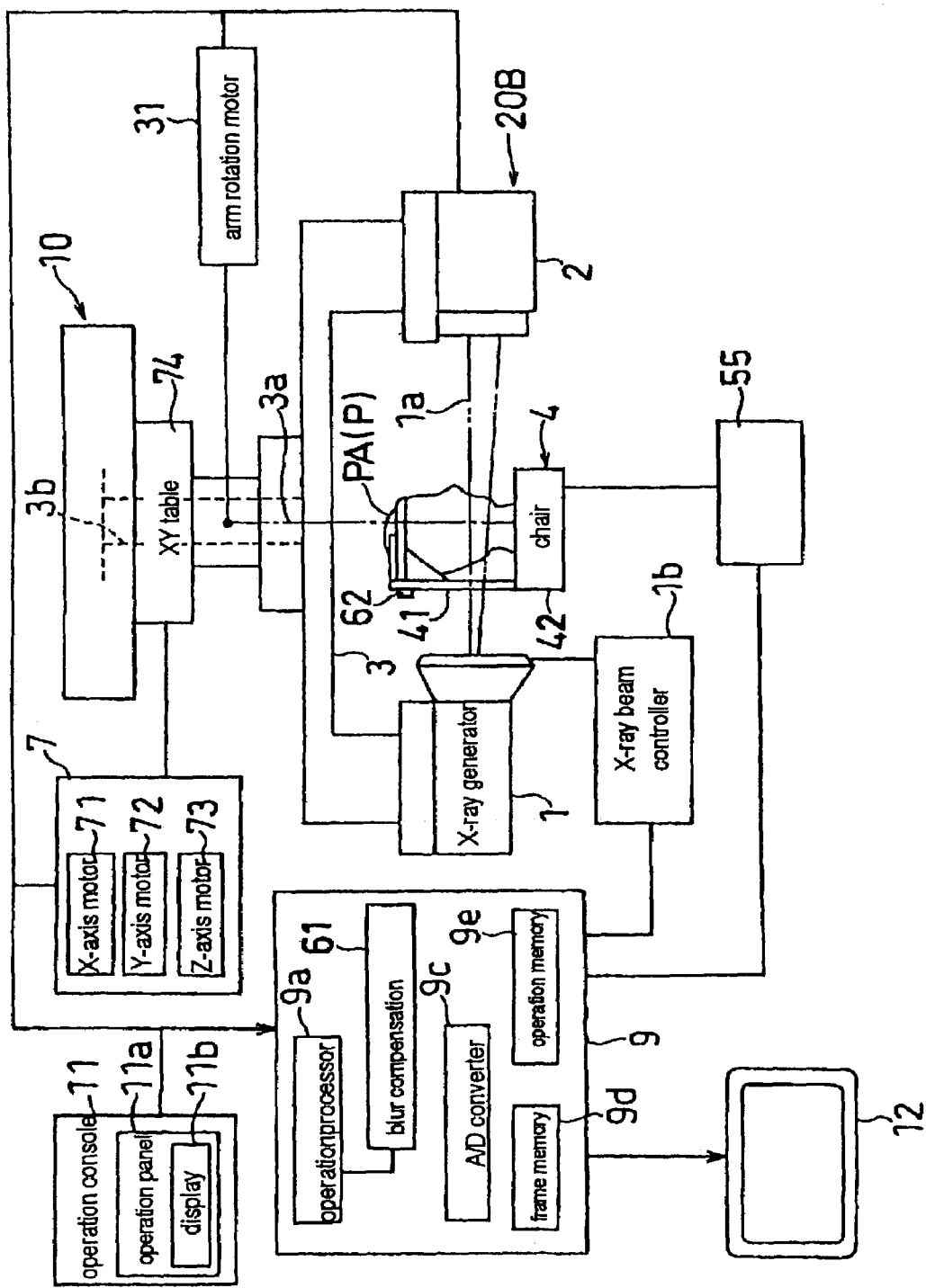
FIG. 9 shows an entire construction of other embodiment of the medical X-ray imaging apparatus according to the present invention.

FIG. 9 shows an entire construction of other embodiment of the medical X-ray imaging apparatus according to the present invention.

The medical X-ray imaging apparatus 20A doesn't have the object moving means 5 unlike the X-ray imaging apparatus 20 in FIG. 6. Those apparatuses are different in that the object holding means 4 of the apparatus 20A only has a motor 55 for moving the head fixing part 41 up and down against the chair 42.

They are also different in that the apparatus 20A has a rotation center moving means 7 having an XYZ table 74 supporting the rotary arm 3, an X-axis motor 71, a Y-axis motor 72 and a Z-axis motor 73 for moving the XYZ table 74 in X, Y, and Z directions respectively.

The construction of the X-axis motor 71, the Y-axis motor 72, and the Z-axis motor 73 of the rotation center moving means 7 is the same as that of the X-axis motor 51, the Y-axis motor 52 and the Z-axis motor 53 of the object moving means 5. The XYZ table 74 is constructed such that three pairs of male and female rails 51c and 51d, 52c and 52d, 53c and 53d are combined so as to accurately slide the supported rotary arm 3 in X, Y, and Z directions.

The imaging apparatus 20A is provided with the above-mentioned rotation center moving means 7 to execute a tomography on a curved plane by moving the X-ray rotation center 3a of the rotary arm 3 during rotational radiation.

Comparing with the imaging apparatus 20 in which the object is moved, an X-ray tomography and an X-ray CT can be executed like the apparatus 20 while moving the X-ray rotation center 3a during X-ray radiation.

According to such an apparatus 20A, the object image blur movement is scarcely caused because the object isn't moved. However, it requires irradiation in a fixed time so that object image blur movement can't be prevented because the object is human. Therefore, the object image blur movement compensation is required and its function is effectively achieved.

EFFECT OF THE INVENTION

Now the effect of the present invention will be explained.

One embodiment of the blur compensation apparatus for X-ray image according to the present invention has the sensor means for detecting an object image blur movement around the objective projection position on the object holding means, thereby detecting the positional change at the objective projection position for the reference position of the object holding means. In other words, the sensor means is provided around the objective projection position on the object holding means, not for the object, so that the sensor means isn't required to be replaced per each object, resulting in saving of labor.

In addition the three-dimensional variation at the objective projection position can be detected by thus detecting the positional change at the objective projection position, thereby enabling to execute a blur compensation process in more multidimensional using the data comparing with the prior art.

Further, the sensor means is provided for the object holding means for holding and moving the object in case of moving the object, therefore, the sensor means is moved together with the object and the relative blur movement of the object against the object holding means can be always detected. Hence, even when the object is moved, the blur movement at the objective projection position can be detected without being affected by the whole movement of the object.

Because the sensor means is provided for the object holding means, other preparation isn't required than positioning of the object at a projection start position, thereby reducing the burden of an operator. In addition, detection means need not to be provided other position than the object holding means, so that the system can be made compact.

If an acceleration sensor, an angular speed sensor, and an angle sensor which can execute a two-dimensional or a three-dimensional detection are used for the sensor means, more accurate and compact construction can be achieved.

In those cases, the sensor means preferably detect two-dimensionally or three-dimensionally in the directions orthogonal each other. One sensor means capable of two-dimensional detection or three-dimensional detection may be provided or plural sensor means capable of two-dimensional detection or three-dimensional detection may be provided.

According to other embodiment of the blur compensating apparatus of the present invention, the projected X-ray images are expanded in a series of image flames, the detection signal of the sensor means is allotted for each frame, and an image blur and the zoom rate are processed per each frame so that an X-ray radiography and a blur compensation process can be executed separately, thereby being applicable for the next process.

In other embodiment of the blur compensation apparatus for X-ray image according to the present invention, the acceleration sensor is used as the sensor means to detect the acceleration at the objective projection position and the acceleration is considered to be an external force applied on the objective projection position, not being integrated, and the structure defining the objective projection position as a beam structure, so that the deflection caused on the beam structure by the external force is determined as the positional change at the objective projection position. Therefore, the deflection of the beam structure, namely the positional change at the objective projection position, is easily calculated by the calculation formula of the beam deflection without executing difficult integration.

Further, two acceleration sensors are used into two different directions respectively so that the two-dimensional blur movement is accurately detected without executing difficult image processing for detecting the blur movement. In addition, the sensors are usually very small one capable of mounting on a fingertip, thereby enabling the apparatus more compact.

In case of detecting the three-dimensional blur movement other than the two-dimensional blur movement, all necessary is adding one sensor. Therefore, the apparatus can be constructed more compact comparing with the construction providing plural TV cameras. Angular speed sensor and an angle sensor may be provided similarly.

As mentioned above, if the acceleration sensor is a three-axis type, only one sensor is provided, thereby achieving down sizing.

In this blur compensation apparatus for X-ray image, the acceleration sensor is provided in two directions, more preferably in two directions orthogonal each other, concretely in two directions orthogonal in a horizontal direction, or in two directions orthogonal a moving plane during radiography while an object and an imaging system comprised of an X-ray imaging device and an X-ray generator are relatively moved, thereby enabling a two-dimensional blur compensation process.

The acceleration sensor is provided in three directions if necessary.

The other embodiment of the blur compensation apparatus for X-ray image according to the present invention is the same as the above-mentioned embodiment in that the structure defining the objective projection position is considered to be a beam construction. However, in this embodiment, the sensor means is comprised of an angular speed sensor. The angular speed sensor detects the angular speed of an angle of inclination at the objective projection position to obtain the angle of inclination at the objective projection position by integration. Further, the positional change at the objective projection position is calculated, thereby facilitating the arithmetic operation.

The other embodiment of the blur compensation apparatus for X-ray image according to the present invention is also the same as the above-mentioned embodiment in that the structure defining the objective projection position is considered to be a beam construction. However, in this embodiment, the sensor means is comprised of an angle sensor. The angle sensor detects the angle of inclination at the objective projection position. Then, the positional change at the objective projection position is calculated, thereby facilitating the arithmetic operation.

According to the other embodiment of the blur compensation apparatus of the present invention, because at least the two-dimensional positional change at the objective projection position is calculated by the sensor means, the positional change is reconstructed to calculate the blur movement of an X-ray image on an imaging plane of the X-ray imaging device and in a direction orthogonal to the plane direction, namely the zoom rate blur of an X-ray image, thereby enabling the image blur compensation process. Therefore, the two-dimensional blur compensation process, which has been difficult in the prior art, becomes possible.

According to the other embodiment of the blur compensation apparatus for X-ray image of the present invention, the object holding means is practically defined wherein the setting position of the sensor means is on the head fixing part and the reference position is on the chair. The sensor detects the positional change at the objective projection position which is a human head against the chair so that this compensation apparatus is preferably used for the projection of the head, the jaw, the dental arch, and the tooth for a dental purpose.

One embodiment of the medical X-ray imaging apparatus according to the present invention has the above-mentioned blur compensation apparatus for X-ray image so that it achieves the effects of the compensation apparatus.

According to other embodiment of the medical X-ray imaging apparatus of the present invention, comparing with the above-mentioned apparatus, the object moving means is further provided. Namely, the object is moved (including rotation) during X-ray radiography so that the object image blur movement is often caused. Therefore, the effects of the above-mentioned blur compensation apparatus for X-ray image are achieved more effectively.

The other embodiment of the medical X-ray imaging apparatus of the present invention is a dental apparatus for executing an X-ray radiography of a human head. The apparatus has the blur compensation apparatus for X-ray image corresponding to the X-ray CT and the X-ray panoramic radiography in which the object is moved. The effect such that the X-ray CT and the X-ray panoramic radiography can be unified is more effectively achieved.

According to other embodiment of the medical X-ray imaging apparatus of the present invention, the projected X-ray images are expanded in a series of image flames, the detection signal of the sensor means is allotted for each frame, and an image blur and the zoom rate are processed per each frame so that an X-ray radiography and a blur compensation process can be executed separately, thereby being applicable for the next process.

The invention claimed is:

1. A medical X-ray imaging apparatus comprising a blur compensation apparatus for X-ray image of a head of an object comprising:
    an X-ray generator;
    an X-ray imaging device positioned opposite said X-ray generator;
    an object holding means interposing said object therebetween said X-ray generator and said X-ray imaging device, wherein
    said object holding means comprising a reference position and a head fixing part for fixing the head of an object near an objective projection position;
    a sensor means for detecting blur movement of said object fixed on said head fixing part; said sensor means moves together with said object during X-ray radiography and detects the positional change amount relative to said reference position of said objective projection position, based on any one of accelerated velocity, angular speed, and angle acted on said object holding means, in two directions on a relative moving plane of said imaging apparatus or in two directions parallel to the imaging plane, defined by at least said object and the imaging device when said X-ray generator and said X-ray imaging device are relatively moved for X-ray radiography producing X-ray image of said object;
    a blur compensation means executes a blur compensation process on a plurality of two dimensional images based on an image blur movement amount and a deviation of zoom rate calculated from said positional change amount respective to at least said two directions detected by said sensor means for compensating the image of the object, and thereafter
    the blur compensation means rearranges and stores a series of X-ray image frames including X-ray image frame of which blur movement is compensated in time series order as in the X-radiography.

2. The blur compensation apparatus as set forth in claim 1, wherein
    said object holding means comprises a head fixing part of an object moving means with a chair for holding said object in sitting position, said head fixing part being provided with said sensor, and said reference point being provided at said chair, and wherein
    said sensor means detects any one of the accelerated velocity, the angular speed, and the angle acted on said object holding means during X-ray radiography for X-ray image of said object when moving said object moving means.

3. A medical X-ray imaging apparatus for obtaining an X-ray CT image and an X-ray panoramic image of an object to be examined, which has an X-ray generator, an X-ray imaging device opposite thereto, said X-ray generator said X-ray imaging device being rotatable around a rotation center, and an object moving means for moving the object holding means for holding the object at least in a direction parallel to the rotation plane of said rotation, wherein said medical X-ray imaging apparatus has said blur compensation apparatus as set forth in claim 2.

4. The blur compensation apparatus as set forth in claims 1 or 2, wherein said sensor means comprises two acceleration sensors for detecting the accelerated velocity at said objective projection position with respect to said reference position for two directions orthogonal to each other on a moving plane during X-ray radiography, and wherein said positional change amount is calculated by executing a dynamic processing based on the acceleration data detected by said two acceleration sensors.

5. The blur compensation apparatus as set forth in claims 1 or 2, wherein said sensor means comprises two angular speed sensors for detecting the angular speed of said objective projection position with respect to said reference position for two directions orthogonal to each other on a moving plane during X-ray radiography, and wherein said positional change amount is calculated from the angular speed data detected by said two angular speed sensors.

6. The blur compensation apparatus as set forth in claims 1 or 2, wherein said sensor means comprises two angle sensors for detecting an angle of inclination of said objective projection position for said reference position for two directions orthogonal to each other on a moving plane during X-ray radiography, and wherein said positional change amount is calculated from the angle data detected by said two angle sensors.

7. A medical X-ray imaging apparatus for producing an X-ray image of an object to be examined which has an X-ray generator and an X-ray imaging device opposite thereto, said X-ray generator and said X-ray imaging device interposing therebetween said object held by an object holding means; wherein said X-ray imaging apparatus has said blur compensation apparatus as set forth in claim 1.

8. The medical X-ray imaging apparatus as set forth in claim 7, wherein said medical X-ray imaging apparatus further comprises an object moving means for moving said object holding means depending on the purpose of X-ray radiography.

* * * * *